(12) United States Patent
Rolfsvåg et al.

(10) Patent No.: US 12,366,159 B2
(45) Date of Patent: Jul. 22, 2025

(54) SENSOR ASSEMBLY AND SYSTEM, AND A METHOD OF DETERMINING THE FREE WATER LEVEL IN A HYDROCARBON RESERVOIR

(71) Applicant: HYDROPHILIC AS, Tananger (NO)

(72) Inventors: Trond Arne Rolfsvåg, Tananger (NO); Harald Syse, Røyneberg (NO); Øivind Godager, Sandefjord (NO); Solveig Riisøen, Olsvik (NO); Kjetil Ormark Cleveland, Stavanger (NO)

(73) Assignee: Hydrophilic AS, Tananger (NO)

( * ) Notice: Subject to any disclaimer, the term of this patent is extended or adjusted under 35 U.S.C. 154(b) by 0 days.

(21) Appl. No.: 18/546,708

(22) PCT Filed: Feb. 22, 2022

(86) PCT No.: PCT/NO2022/050047
§ 371 (c)(1),
(2) Date: Aug. 16, 2023

(87) PCT Pub. No.: WO2022/182244
PCT Pub. Date: Sep. 1, 2022

(65) Prior Publication Data
US 2024/0133290 A1    Apr. 25, 2024
US 2024/0229639 A9    Jul. 11, 2024

(30) Foreign Application Priority Data
Feb. 23, 2021   (NO) .................................. 20210240

(51) Int. Cl.
*E21B 47/047*  (2012.01)
*E21B 47/06*  (2012.01)
(52) U.S. Cl.
CPC ............ *E21B 47/047* (2020.05); *E21B 47/06* (2013.01)

(58) Field of Classification Search
CPC ........ E21B 47/047; E21B 47/06; E21B 49/00; E21B 47/04; E21B 49/08; E21B 49/081;
(Continued)

(56) References Cited

U.S. PATENT DOCUMENTS 6,234,257 B1 * 5/2001 Ciglenec ................. E21B 47/01
166/250.01
2005/0257611 A1   11/2005 Fogal et al.
(Continued)

FOREIGN PATENT DOCUMENTS

CN      110118808 A    8/2019
EP        0638169 B1    7/1997

OTHER PUBLICATIONS

International Search Report issued in International Patent Application No. PCT/NO2022/050047, dated Apr. 28, 2022 in 4 pages.
(Continued)

*Primary Examiner* — Yanick A Akaragwe
(74) *Attorney, Agent, or Firm* — Knobbe Martens Olson & Bear LLP

(57) ABSTRACT

A sensor system and method for determining the vertical distance between a location (L) in a hydrocarbon reservoir (R) in a subterranean formation (F) and the free water level (FWL) in said reservoir. A sensor assembly (10; 10'; 10''; 10''') is configured for installation at a location (L) in a reservoir and comprises at least one sensor (11) in contact with or at least partly embedded in a porous material (13). At last a portion of the porous material comprises pores having hydrophilic surfaces, and the sensor is configured for measuring the water content in the porous material. Means are provided for determining the water saturation ($S_W$) of the porous material and for estimating a pressure difference ($P_D$) between the hydrocarbon pressure and the water pressure.

16 Claims, 4 Drawing Sheets

(58) Field of Classification Search
CPC ..... E21B 49/087; E21B 49/10; G01N 27/221; G01N 33/241; G01F 23/26
See application file for complete search history.

(56) References Cited

U.S. PATENT DOCUMENTS

| | | |
|---|---|---|
| 2013/0045902 A1 | 2/2013 | Thompson et al. |
| 2015/0198036 A1 | 7/2015 | Kleinberg et al. |
| 2017/0241934 A1 | 8/2017 | Goodchild et al. |
| 2017/0276822 A1* | 9/2017 | Ewe .......................... G01V 3/30 |
| 2019/0323339 A1* | 10/2019 | Rolfsvåg ................. E21B 49/10 |
| 2020/0319011 A1 | 10/2020 | Brewer et al. |

OTHER PUBLICATIONS

Norwegian Search Report issued in Norwegian Patent Application No. 20210240, dated Nov. 22, 2021 in 2 pages.

* cited by examiner

SENSOR ASSEMBLY AND SYSTEM, AND A METHOD OF DETERMINING THE FREE WATER LEVEL IN A HYDROCARBON RESERVOIR

CROSS-REFERENCE TO RELATED APPLICATIONS

This application is the U.S. National Phase under 35. U.S.C. § 371 of International Application PCT/NO2022/050047, filed Feb. 22, 2022, which claims priority to Norwegian Patent Application No. 20210240, filed Feb. 23, 2021. The disclosures of the above-described applications are hereby incorporated by reference in their entirety.

TECHNICAL FIELD OF THE INVENTION

The invention concerns the exploration and production of oil and gas from subterranean reservoirs. More specifically, the invention is related to a sensor assembly, a sensor system, and a method of determining the free water level in a subterranean hydrocarbon reservoir, as set out by the preamble of claims 1, 8, and 13, respectively.

BACKGROUND OF THE INVENTION

Subterranean hydrocarbon reservoirs are normally found in or adjacent to aquifers. FIG. 1 is a schematic illustration of a reservoir R extending downwards in a formation from an upper boundary $R_T$ and comprising a hydrocarbon (e.g. oil) zone $Z_{HC}$ and a water zone $Z_W$. In the hydrocarbon zone, the hydrocarbon pressure is greater than the water pressure ($P_{HC} > P_W$), and vice versa in the water zone. A transition zone extends upwards from the hydrocarbon-and-water interface (Hydrocarbon-Water Contact: HWC). The HWC occurs where the hydrocarbon pressure equals the sum of local formation pore entry pressure and the formation water pressure ($P_{HC} = P_E + P_W$). The FWL occurs at the level where the hydrocarbon pressure equals the water pressure ($P_{HC} = P_W$). Above the FWL, the reservoir may produce water, hydrocarbons, or a mixture of hydrocarbons and water. Determining the HWC and the FWL when producing hydrocarbons from a subterranean reservoir is of great importance in order to avoid water production.

FIG. 1 illustrates a subterranean hydrocarbon reservoir in equilibrium, i.e. a static state in which the isobars are substantially horizontal. Therefore, FWL determined on the basis of measurements at one location (e.g. in well $W_A$), may be representative for the FWL at other locations within the same reservoir, such as at the well $W_B$.

However, once production of hydrocarbons commences, often through multiple wells in the same reservoir and supported by natural aquifers or by injection of water, the interface between hydrocarbons and water becomes more complex, and it may be difficult to determine how the hydrocarbon column is shrinking with time. FIG. 2 is a simplified and schematic illustration of a hydrocarbon reservoir a dynamic state, illustrating how the isobars are inclined. It should be understood that the isobars may have other inclinations than illustrated, as well as non-linear inclinations. The shape and properties of the underground formation may not be well known, and the water may invade the hydrocarbon reservoir in unpredictable ways. This makes it difficult to plan good locations for future wells, and may lead to drilling of wells that produce excessive amounts of water, add little value, and that might have to be re-drilled or permanently abandoned. Significant data collection is done to improve the prediction of the water movement. It is therefore a need for a system and method for more precisely determining the FWL at a desired location, as well as its variation over time.

SUMMARY OF THE INVENTION

The invention is set forth and characterized in the main claims, while the dependent claims describe other characteristics of the invention.

It is thus provided a sensor assembly configured for installation at a location in a hydrocarbon reservoir in a subterranean formation, characterized by
  a porous material;
  at least one sensor for measuring the water content in said porous material by utilizing the difference in dielectric constant between hydrocarbon and water;
  wherein said porous material comprises pores having hydrophilic surfaces and has been selected based on desired properties.

In one embodiment, the porous material properties are dependent on the properties of the reservoir and may comprise pore size and distribution, or pore surface properties. The relationship between water saturation and pressure difference in the porous material is preferably known.

In one embodiment, the at least one sensor is attached to or at least partly embedded in the porous material. The porous material may comprise a porous member, such as a ceramic member. In one embodiment, the porous member is shaped as a disk, a cylinder, a sphere, or a pellet. In one embodiment, the sensor assembly comprises a plurality of porous members and a corresponding plurality of sensors.

It is also provided a sensor system for determining the vertical distance between a location in a hydrocarbon reservoir in a subterranean formation and the free water level in said reservoir, characterized by:
  a sensor assembly according to the invention;
  a power and control module electrically connected to the sensor and comprising means for determining the water saturation of said porous material and means for estimating a pressure difference between the hydrocarbon pressure and the water pressure, based on said determined water saturation, and for calculating said vertical distance based on said pressure difference. Said means may comprise information about the porous material, at least information about the pore size distribution of at least a portion of the porous material. Said means may comprise computing means for establishing the relationship between water saturation and pressure difference for the porous material. In one embodiment, the sensor system comprises a water injection device for introducing water into at least a portion of the porous material. The sensor may comprise a dielectric sensor.

It is also provided a method of determining the vertical distance between a location in a hydrocarbon reservoir in a subterranean formation and the free water level in said reservoir, characterized by:
  a) selecting a porous material with pores having hydrophilic surfaces, based on desired properties;
  b) determining the water saturation in a porous material at or in the region of said location, by utilizing the difference in dielectric constant in water and hydrocarbon;
  c) estimating the pressure difference between the hydrocarbon pressure and the water pressure, based on said determined water saturation, and d) calculating said vertical distance based on said pressure difference.

In one embodiment, step a of the method comprises establishing the relationship between water saturation and pressure difference and by determining the pore size distribution of the porous material. The method may further comprise introducing water into at least a portion of the porous material following step c. The method may be executed by the sensor system according to the invention.

The invented invention enables an operator of a hydrocarbon reservoir in obtaining precise knowledge of the water levels in the reservoir, and thus provides the operator with a tool for optimizing the production of existing well, for more precise positioning of future wells. Precise knowledge of the water movement in the reservoir might result in a more cost-efficient operation with less environmental impact.

BRIEF DESCRIPTION OF THE DRAWINGS

These and other characteristics of the invention will become clear from the following description of embodiments of the invention, given as non-restrictive examples, with reference to the attached schematic drawings, wherein:

FIG. 3a illustrating water saturation at a lower pressure difference and FIG. 3b illustrating water saturation at a higher pressure difference;

DETAILED DESCRIPTION OF EMBODIMENTS OF THE INVENTION

Figure 1:
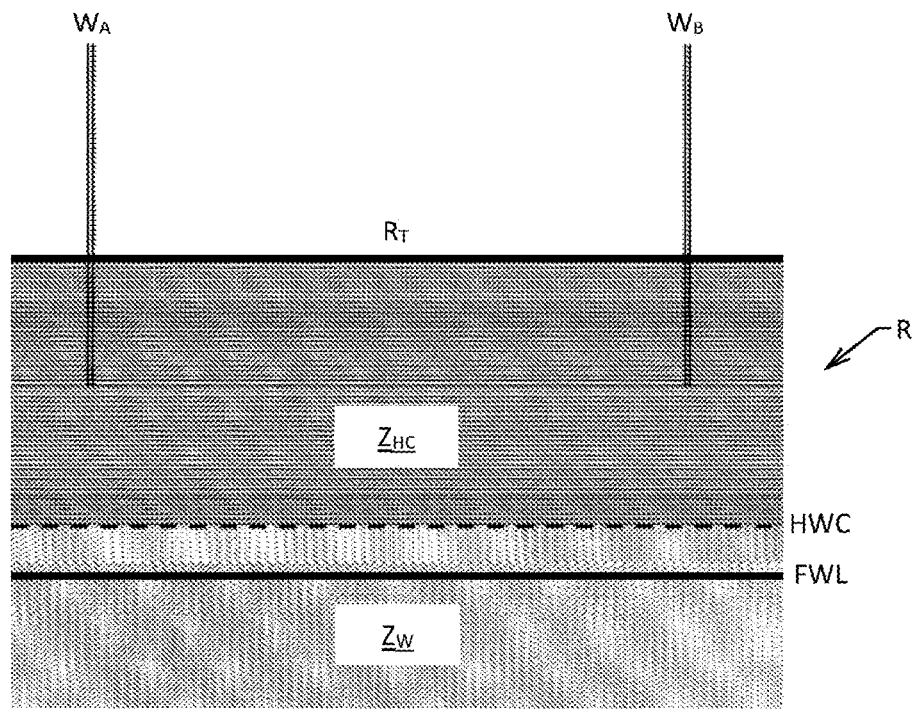
FIG. 1 is an illustration of a hydrocarbon reservoir in equilibrium.
Figure 2:
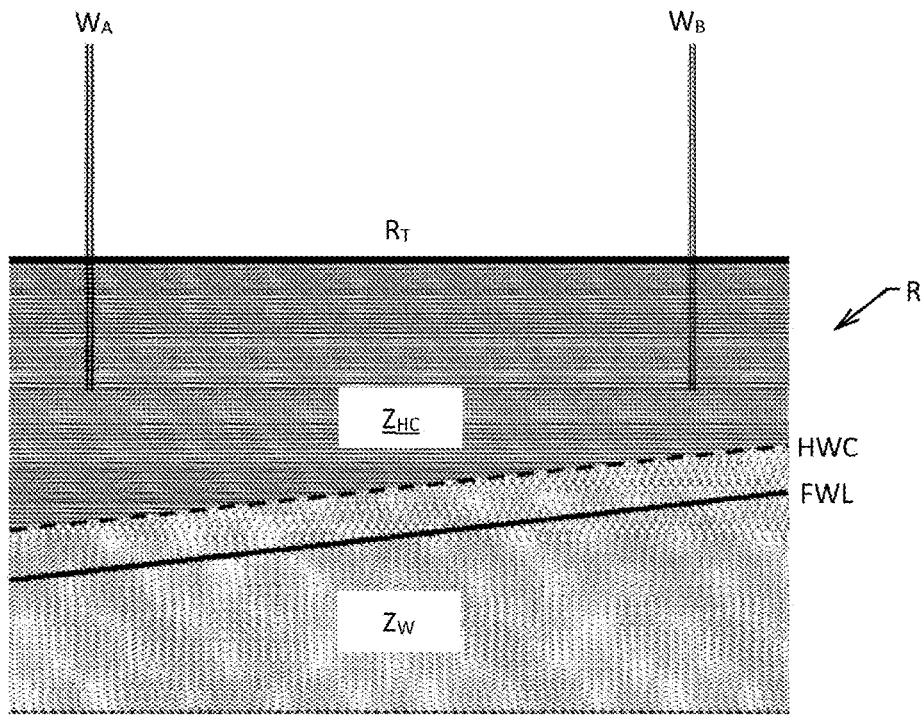
FIG. 2 is an illustration of a hydrocarbon reservoir in a dynamic state.

The following description may use terms such as "horizontal", "vertical", "lateral", "back and forth", "up and down", "upper", "lower", "inner", "outer", "forward", "rear", etc. These terms generally refer to the views and orientations as shown in the drawings and that are associated with a normal use of the invention. The terms are used for the reader's convenience only and shall not be limiting.

One aspect of the invention is to use the water saturation level as measured in a porous material to estimate the vertical column of hydrocarbons below the material, i.e. the vertical proximity of water (distance to FWL).

In a reservoir in a state of equilibrium, the pressure difference $P_D$ between the hydrocarbon phase pressure $P_{HC}$ and water phase pressure $P_W$ gives a measure of the distance to the FWL in the reservoir. In a producing reservoir, $P_D$ (i.e. $P_D = P_{HC} - P_W$) is mostly dynamic, for example for the reasons discussed above. It might take too long to wait for equilibrium to occur, but with pressure difference measurements that can be done over time in multiple locations in the field, a dynamic situation can be monitored continuously.

The invention is not based on direct measurements of $P_D$, but involves estimating this pressure difference based on the water saturation $S_W$ in a porous material having known properties and known performance, at a known point in the reservoir. When $P_D$ has been thus estimated, the vertical distance between the location in the formation at which $S_W$ is measured and the FWL may be calculated in a manner known in the art. This calculation relies on the fact that the density of water is greater than the density of hydrocarbons, and thus that the two substances exhibit different pressure gradients with vertical depth. Calculating the intersection (i.e. $P_D = 0$) between the two pressure gradients determines the FWL.

Figure 3:
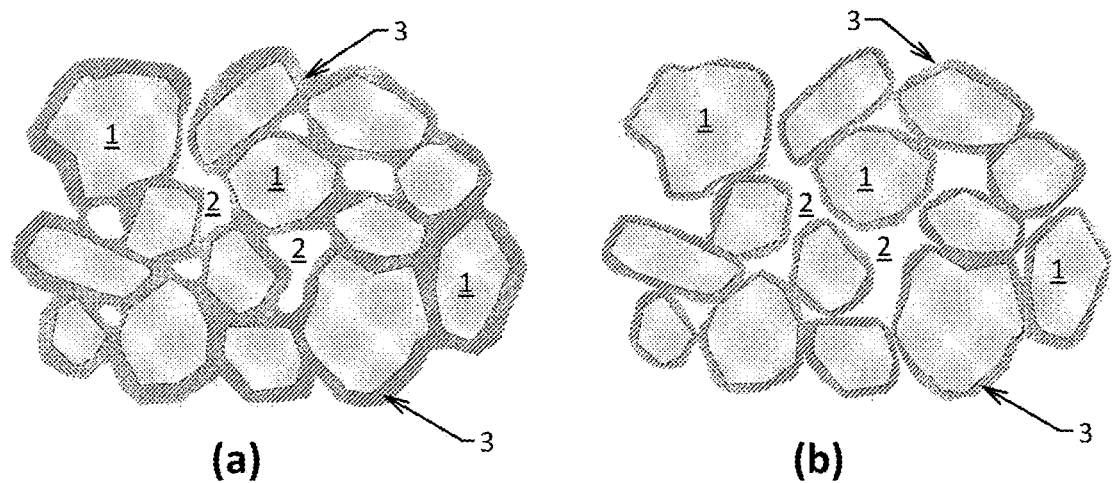
FIG. 3 is an illustration of water saturation in a material having pores with hydrophilic surfaces, at different pressure differences between hydrocarbon and water.

In a porous material, particularly a porous material having hydrophilic surfaces, water will have affinity towards the surfaces. The polarity of water and the polar sites on the surface attract each other. FIG. 3 illustrates this principle. The figure is a schematic representation of a porous material with hydrophilic surfaces, i.e. a combination of solid elements or particles 1 and pores 2.

Water molecules are attracted to the particles or grains 1 and form a film 3 of water (grey regions in FIG. 3) on the grain surfaces. When the water film 1 is continuous, pressure can equilibrate throughout this film. If the hydrocarbon phase has no over-pressure i.e., no vertical column thickness, all the pores will be filled with water. The white areas in FIG. 3 represent the non-wetting hydrocarbon phase. The hydrocarbon phase must have a higher pressure to be present in the porous material as a continuous phase. The water film on the surface of the grains becomes thinner, and the water saturation becomes lower, as the hydrocarbon over-pressure increases (increasing $P_D$). The amount of water in such a system therefore becomes a measure of the hydrocarbon over-pressure. FIG. 3a illustrates $S_W$ at a lower $P_D$, while FIG. 3b illustrates $S_W$ at a higher $P_D$.

Figure 4:
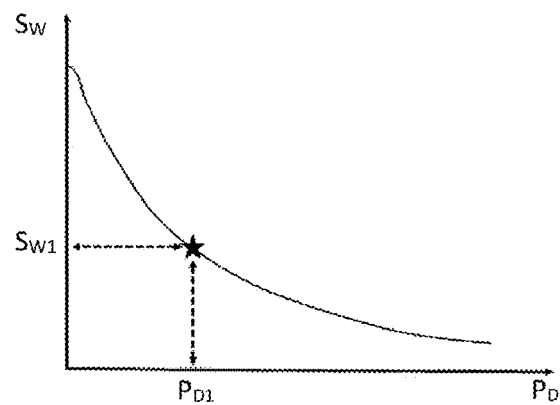
FIG. 4 is a plot of water saturation as a function of pressure head, and thus illustrates a relationship between pressure difference and water saturation.
Figure 5:
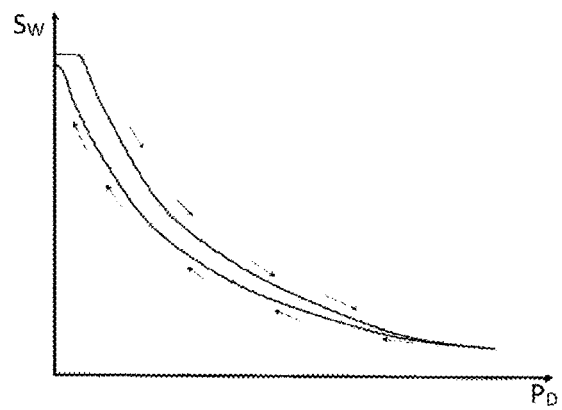
FIG. 5 corresponds to FIG. 4, and illustrates a hysteresis effect that may be observed during increasing and decreasing pressure differences, e.g. during a calibration.
Figure 6:
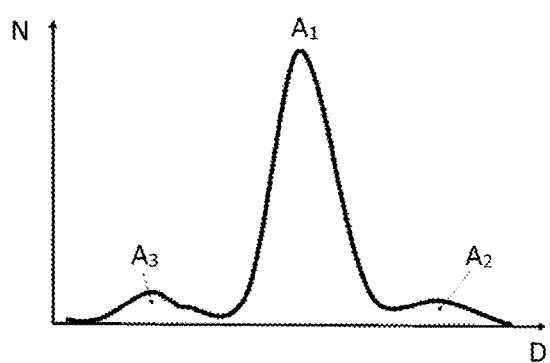
FIG. 6 is a plot of pore size distribution in a porous material.

This relationship between $S_W$ and $P_D$ is illustrated in FIG. 4, and shows how a measurement of $S_{W1}$ in a porous material may enable an estimate of the associated $P_{D1}$. However, in a practical application, the relationship between $S_W$ and $P_D$ must be known, measured and calibrated for the material in which $S_W$ is to be measured. This relationship may be different when the pressure difference is increasing, from when the pressure difference is decreasing, i.e. a hysteresis effect is observed (see FIG. 5). The relationship may also be different between the first water saturation decrease and the second decrease. Therefore, for each porous material in which $S_W$ is to be measured, a curve similar to the curve in FIG. 4 needs to be established. In addition to knowledge of the relationship between hydrocarbon and water saturation as a function of pressure difference between the hydrocarbon phase and water, knowledge of the pore size distribution is necessary in order to form this "calibration curve" for a specific material. The amount of water-filled pores is a measure of the vertical downward distance between the porous material (where the measurement is made) and water. FIG. 6 is a schematic plot of number of pores N in relation to pore size D. The pore size distribution may comprise various ranges, for example a first range $A_1$ having a first pore size distribution, a second range $A_2$ having a number of larger pores that are sensitive to small columns of hydrocarbon (pores become filled when water is close to the pores), and a third range $A_3$ having a number of smaller pores that are smaller to be able to tell when the hydrocarbon column is starting to shrink (i.e., approaching the sensor but still at a significant vertically downward distance away). The smaller pores will be filled with oil only when water is far below the porous material.

The shape and accuracy of the calibration curve (e.g. as shown in FIG. 4) determines the precision of the estimate of $P_D$ based on the measurement of $S_W$ in the porous material. The porous material (or materials) therefore advantageously has a porosity distribution that results in a calibration curve that can distinguish between situations where the water is close (only larger pores filled with oil) and situations when the water is far away vertically (both larger and smaller pores filled with oil).

The invented sensor assembly 10 comprises a sensor 11 that is in physical contact with a porous material. The sensor assembly 10 and associated power systems, control systems, data analysis means, and one or more user interface modules, form a sensor system 12.

Figure 8:
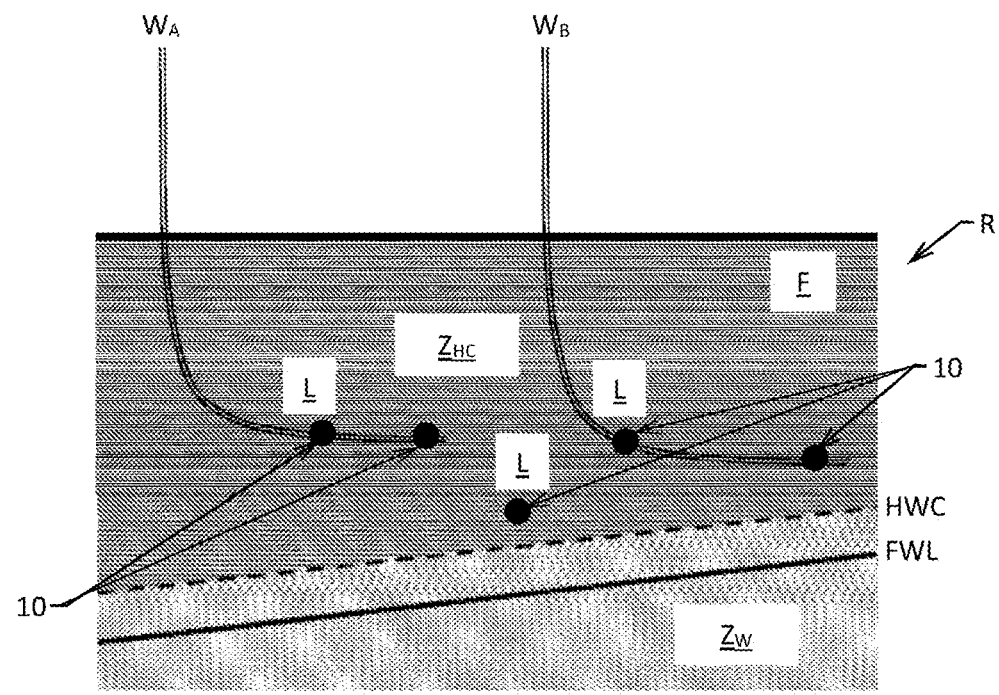
FIG. 8 illustrates a plurality of sensor assemblies according to the invention, installed in hydrocarbon wells in a subterranean formation.

FIG. 8 illustrates that one or more sensor assemblies 10 may be placed at respective locations L in a hydrocarbon reservoir R in a subterranean formation F. Although the figure illustrates horizontal wellbores, it should be understood that the invention is equally applicable for any wellbore orientation. In fact, the sensor assembly may be installed anywhere in the formation, independent of wellbore location and orientation. The sensor assembly may be installed in a manner known in the art, directly into the formation or via a borehole, for example through a casing perforation, and may be forced into the formation or pressed against the formation. The sensor assembly may be shaped to suit the intended method of installation.

Figure 9:
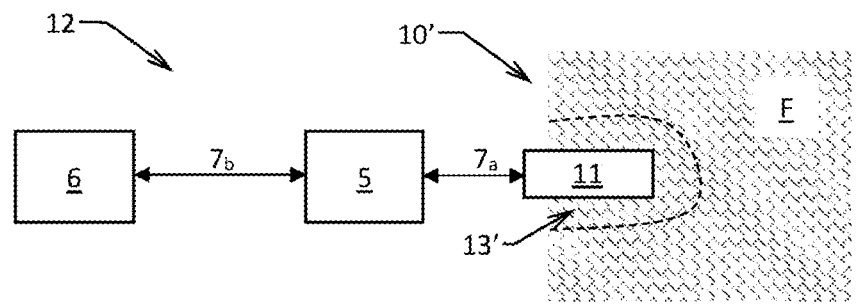
FIG. 9 is a schematic illustration of a first embodiment of the sensor assembly according to the invention, installed in a subterranean formation.

Referring to FIG. 9, the sensor assembly 10' according to a first embodiment of the invention comprises a sensor 11 installed in a porous material 13'. The porous material 13' is in this embodiment a material naturally present in the formation F, as indicated by the dashed line around the sensor 11. This embodiment is useful if the porous material 13' (i.e. the formation F around the sensor 11) has a useful porosity distribution and pore surface properties, as discussed above with reference to FIGS. 3 to 6. A sample may be extracted from the formation to establish its suitability, and to calibrate the sensor assembly as discussed above with reference to FIG. 5.

Figure 10:
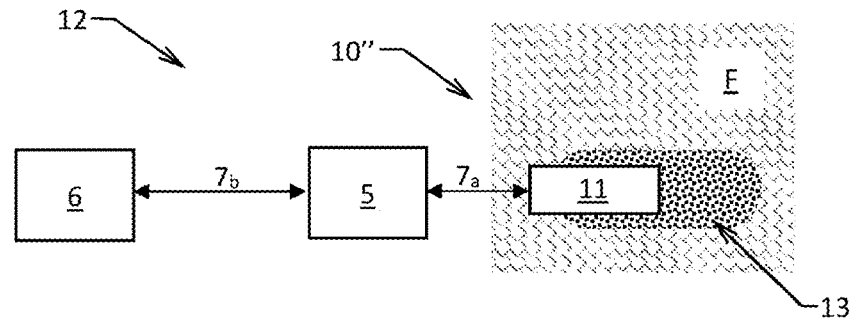
FIG. 10 is a schematic illustration of a second embodiment of the sensor assembly according to the invention, installed in a subterranean formation.

Referring to FIG. 10, the sensor assembly 10" according to a second embodiment of the invention comprises a sensor 11 installed in a porous material 13. The porous material 13 in this embodiment has been selected based on the desired properties (which may be reservoir-dependent), such as porosity size and distribution, pore surface properties, as discussed above with reference to FIGS. 3 to 6. Sensor assembly calibration may be performed as discussed above with reference to FIG. 5.

Measurement of the water saturation $S_W$ in the porous material takes advantage of the relatively large difference in dielectric constant between hydrocarbon and water. In one embodiment, the sensor 11 comprises a dielectric sensor 11. The sensor 11 may be any sensor capable of measuring the water content in a porous material and contribute to the measurement of $S_W$ in the porous material.

The porous material 13 may be a member formed of a ceramic material, or any other material having a suitable pore size and distribution. At least a portion of the porous material 13 has hydrophilic surfaces. The porous material must be selected carefully to be suitable for providing a consistent and reliable relationship between $P_D$ and $S_W$. The porous material 13 may be shaped in any form suitable for the intended purpose, for example as a disc, a pellet, a sphere, a block, or a cylinder. The sensor 11 may be attached to the porous material in any suitable manner. The sensor 11 may be at least partly embedded in the porous material 13 and the sensor and porous material may thus form a unit that may be installed in a subterranean formation F, as shown in FIG. 10. Other configurations are conceivable, as long as the sensor is in physical contact with the porous material.

In FIG. 9 and FIG. 10, the sensor 11 is connected to a power, control and communications module 5 via first communication means $7_a$, and a user interface module 6, comprising i.e. data storage and analysis means, and display and control means, is connected to the module 5 via second communication means $7_b$. The modules 5, 6 are per se known in the art and comprise the necessary means and functionalities to operate the sensor assembly, as well as retrieving and analysing data from the sensors. The modules are preferably located above the subterranean formation, and may be located at different sites. It will be understood that the modules 5, 6 may be connected to one or more sensor assemblies 10. The modules and one or more sensor assembly form a sensor system 12.

Figure 11:
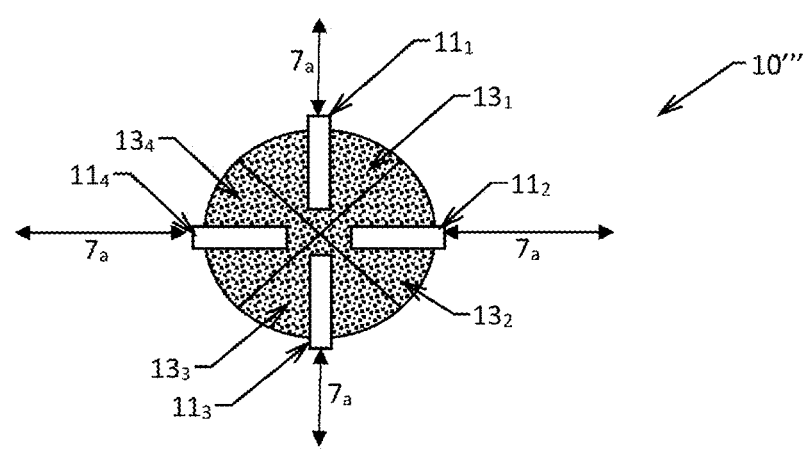
FIG. 11 and FIG. 12 are schematic illustrations of variants of the second embodiment of the sensor assembly.
Figure 12:
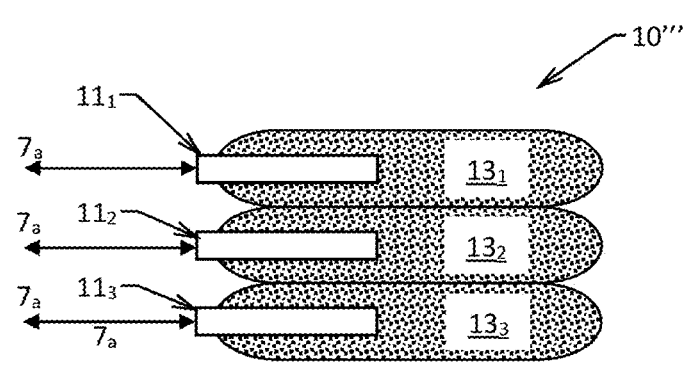

Referring to FIG. 11 and FIG. 12, the sensor assembly 10''' may comprise a plurality of porous materials $13_{1-n}$ having different properties (e.g. pore size, pore distribution), each connected to a respective sensor $11_{1-n}$ in a manner described above. For example, one variant of the sensor assembly may comprise a circular disc having distinct segments $13_{1-4}$ (FIG. 11), and another variant may comprise stacked distinct segments $13_{1-3}$ (FIG. 12).

Figure 7:
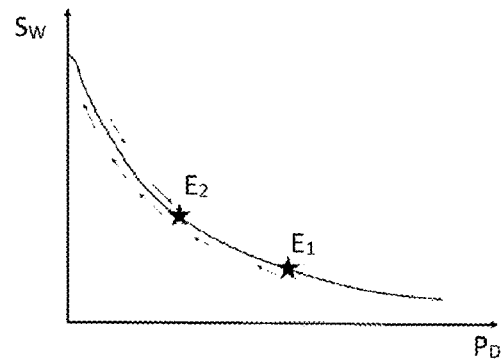
FIG. 7 corresponds to FIG. 4 and illustrates how hydraulic equilibrium may change over time in a hydrocarbon reservoir in a dynamic state.

When using the porous material as described above in a subterranean reservoir during production of hydrocarbons, the hydraulic equilibrium between the reservoir fluids and the porous material tends to change. This is illustrated in FIG. 7, in which $E_1$ designates a state of equilibrium when measurement of $S_W$ is commenced (e.g. when a sensor is installed) and $E_2$ designates a state of equilibrium after a period of time (when hydrocarbons have been produced from the reservoir). Water present in the reservoir high above the HWC may have very low mobility, and a comparably long time may therefore pass before a true state of equilibrium between the reservoir and the porous material is achieved. Therefore, in order to assist and expedite this process towards equilibrium (and thus achieve a shorter response time), water may be introduced (e.g. infused over an extended period of time, or injected momentarily) into the porous material in a quantity sufficient to bring the water saturation in the porous material above equilibrium with the reservoir. This will improve result in a faster and more representative response from the porous material.

Although the invention has been described with reference to application in a subterranean hydrocarbon reservoir and for determining the distance between hydrocarbons and free water level, it should be understood that the invention is equally applicable in other contexts.

In the embodiments described above, various features and details are shown in combination. The fact that several features are described with respect to a particular example should not be construed as implying that those features by necessity have to be included together in all embodiments of the invention. Conversely, features that are described with reference to different embodiments should not be construed as mutually exclusive. As a person skilled in the art readily will understand, embodiments that incorporate any subset of features described herein and that are not expressly interdependent have been contemplated by the inventor and are part of the intended disclosure. However, explicit description of all such embodiments would not contribute to the understanding of the principles of the invention, and consequently some permutations of features have been omitted for the sake of simplicity or brevity.

What is claimed is:

1. A sensor assembly configured for installation at a location in a hydrocarbon reservoir in a subterranean formation, said sensor assembly comprising:
   a porous material;
   at least one sensor arranged in physical contact with the porous material and configured for measuring water content in said porous material by utilizing a difference in dielectric constant between hydrocarbon and water;
   wherein said porous material comprises pores having hydrophilic surfaces and has been selected based on desired properties; and
   wherein the sensor assembly is forced into the formation or pressed against the formation.

2. The sensor assembly of claim 1, wherein said porous material properties are dependent on the properties of the reservoir and may comprise pore size and distribution, or pore surface properties.

3. The sensor assembly of claim 1, wherein a relationship between water saturation and pressure difference in the porous material is known.

4. The sensor assembly of claim 1, wherein the at least one sensor is attached to or at least partly embedded in the porous material.

5. The sensor assembly of claim 1, wherein the porous material comprises a porous member.

6. The sensor assembly of claim 5, wherein the porous member is shaped as a disk, a cylinder, a sphere, or a pellet.

7. The sensor assembly of claim 5, comprising a plurality of porous members and a corresponding plurality of sensors.

8. The sensor assembly of claim 5, wherein the porous member comprises a ceramic member.

9. A sensor system for determining a vertical distance between a location in a hydrocarbon reservoir in a subterranean formation and a free water level in said reservoir, comprising:
   a sensor assembly as defined by claim 1;
   a power and control module electrically connected to the at least one sensor and comprising a device for determining a water saturation of said porous material and for estimating a pressure difference between hydrocarbon pressure and water pressure, based on said determined water saturation, and for calculating said vertical distance based on said pressure difference.

10. The sensor system of claim 9, wherein said device comprises information about the porous material, at least information about a pore size distribution of at least a portion of the porous material.

11. The sensor system of claim 9, wherein said device comprises a computing device for establishing a relationship between water saturation and pressure difference for the porous material.

12. The sensor system of claim 9, wherein at least a portion of the porous material is configured for water injection.

13. The sensor system of claim 9, wherein the at least one sensor comprises a dielectric sensor.

14. A method of determining a vertical distance between a location in a hydrocarbon reservoir in a subterranean formation and a free water level in said reservoir, comprising:
   a1) selecting a porous material with pores having hydrophilic surfaces, based on desired properties;
   a2) installing the sensor assembly as defined by claim 1, wherein the porous material of the sensor assembly as defined by claim 1 is a porous material as selected in step a1, at a location in a hydrocarbon reservoir in a subterranean formation, and forcing the sensor assembly into the formation or pressing the sensor assembly against the formation;
   b) determining a water saturation in the porous material at or in a region of said location, by utilizing the difference in dielectric constant in water and hydrocarbon;
   c) estimating a pressure difference between hydrocarbon pressure and water pressure, based on said determined water saturation, and
   d) calculating said vertical distance based on said pressure difference.

15. The method of claim 14, wherein step a1) comprises establishing a relationship between water saturation and pressure difference and determining a pore size distribution of the porous material.

16. The method of claim 14, further comprising introducing water into at least a portion of the porous material following step c.

* * * * *